(12) United States Patent
Freeman

(10) Patent No.: US 10,779,494 B2
(45) Date of Patent: Sep. 22, 2020

(54) CARROT VARIETY NUN 89853 CAC

(71) Applicant: NUNHEMS B.V., Nunhem (NL)

(72) Inventor: Roger E. Freeman, Brooks, OR (US)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/281,456

(22) Filed: Feb. 21, 2019

(65) Prior Publication Data

US 2019/0183083 A1    Jun. 20, 2019

Related U.S. Application Data

(60) Provisional application No. 62/633,147, filed on Feb. 21, 2018.

(51) Int. Cl.
*A01H 5/06* (2018.01)
*A01H 6/06* (2018.01)

(52) U.S. Cl.
CPC .............. *A01H 6/068* (2018.05); *A01H 5/06* (2013.01)

(58) Field of Classification Search
None
See application file for complete search history.

(56) References Cited

U.S. PATENT DOCUMENTS

| | | | | |
|---|---|---|---|---|
| 2013/0260011 A1* | 10/2013 | Freeman | ............ | C12N 15/8241 426/635 |
| 2015/0126380 A1 | 5/2015 | Van Dun | | |
| 2015/0245570 A1 | 9/2015 | Vogelaar et al. | | |

OTHER PUBLICATIONS

"Guidelines for the Conduct of Tests for Distinctness, Uniformity and Stability", TG/49/8, UPOV, International Union for the Protection of New Varieties of Plants, Geneva, UPOV Code: DAUCU_CAR, Mar. 28, 2007, 32 pages.
"Objective Description of Variety Carrot (*Daucus carota*)", US Department of Agriculture, Agricultural Marketing Service Science and Technology Plant Variety protection office, 2015, 4 pages.
Arnholdt-Schmitt et al., "Physiological aspects of genome variability in tissue culture. I. Growth phase-dependent differential DNA methylation of the carrot genome (*Daucus carota* L.) during primary culture", Theoretical and Applied Genetics, vol. 91, Issue 5, Oct. 1995, pp. 809-815.
Jhang et al., "Efficiency of different marker systems for molecular characterization of subtropical carrot germplasm", The Journal of Agricultural Science, vol. 148, Issue 2, Apr. 2010, pp. 171-181.
Larkin et al., "Somaclonal variation—a novel source of variability from cell cultures for plant improvement", Theoretical and Applied Genetics, vol. 60, Issue 4, Oct. 1981, pp. 197-214.
Martin et al., "Identification of markers linked to agronomic traits in globe artichoke", Australian Journal of Crop Science, vol. 1, Issue 2, 2008, pp. 43-46.
Needleman et al., "A general method applicable to the search for similarities in the amino acid sequence of two proteins", Journal of Molecular Biology, vol. 48, Issue 3, Mar. 28, 1970, pp. 443-453.
Nikolova et al., "Diploidization of cucumber (*Cucumis sativus* L.) haploids by colchicine treatment", Acta Societatis Botanicorum Poloniae, vol. 65, Issue 3-4, 1996, pp. 311-317.
Rice et al., "EMBOSS: the European Molecular Biology Open Software Suite", Trends in Genetics, vol. 16, Issue 6, Jun. 2000, pp. 276-277.
Shim et al., "Genetic structure in cultivated and wild carrots (*Daucus carota* L.) revealed by AFLP analysis", Theoretical and Applied Genetics, vol. 101, Issue 1-2, Jul. 2000, pp. 227-233.
Stein et al., "Some remarks on carrot breeding (*Daucus carota sativus* Hoffm.)", Plant Breeding, vol. 114, Issue 1, Feb. 1995, pp. 1-11.
Vos et al., "AFLP: a new technique for DNA fingerprinting", Nucleic Acids Research, vol. 23, Issue 21, 1995, pp. 4407-4414.
Wijnker et al., "Hybrid recreation by reverse breeding in *Arabidopsis thaliana*", Nature Protocols, vol. 9, 2014, pp. 761-772.

* cited by examiner

*Primary Examiner* — Medina A Ibrahim
(74) *Attorney, Agent, or Firm* — Arent Fox LLP

(57) ABSTRACT

The disclosure provides a new and distinct hybrid carrot variety NUN 89853 CAC as well as seeds and plants and roots thereof.

23 Claims, No Drawings

CARROT VARIETY NUN 89853 CAC

CROSS-REFERENCE TO RELATED APPLICATIONS

This application claims priority to U.S. Provisional Application No. 62/633,147 filed Feb. 21, 2018, which is hereby incorporated by reference in its entirety.

FIELD OF THE DISCLOSURE

The present disclosure relates to the field of plant breeding and, more specifically, to carroty variety NUN 89853 CAC. The disclosure further relates to vegetative reproductions of NUN 89853 CAC, methods for tissue culture of NUN 89853 CAC and regenerating a plant from such a tissue culture, and also to phenotypic variants of NUN 89853 CAC.

BACKGROUND OF THE DISCLOSURE

The goal of vegetable breeding is to combine various desirable traits in a single variety or hybrid. Such desirable traits may include greater yield, resistance to diseases, insects or other pests, tolerance to heat and drought, better agronomic quality, higher nutritional value, enhanced growth rate and improved root properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, optionally three-way hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species which has been subject to such breeding programs and is of particular value is the carrot. Carrot (*Daucus carota* subsp. *sativus*), is a biennial plant that grows a rosette of leaves in the spring and summer, while building up the stout taproot, which stores large amounts of sugars for the plant to flower in the second year. The flowering stem grows several decimeters (e.g., 60-200 cm) tall, with an umbel of white flowers that produce a fruit called a mericarp.

Carrot is grown as a root vegetable, usually orange in color, though purple, red, white, cream, and yellow varieties exist. It has a crisp texture when fresh. The most commonly eaten part of a carrot is the root, although the greens are edible as well. It is a domesticated form of the wild carrot *Daucus carota*, native to Europe and Southwestern Asia. The domestic carrot has been selectively bred for its greatly enlarged and more palatable, less woody-textured edible taproot. Carrots are primarily consumed fresh as snack food, raw vegetable or as salad ingredient. Carrots are also popular as cooking vegetable and can be frozen and juiced.

United States is one of the largest carrot producers in the world. Between 1994 and 2014, an average production of 1.4 million pounds of carrots were produced in the United States (Food and Agriculture Organization (FAO)). Carrots are grown year-round in the United States with the highest volume coming from California from December to August.

While breeding efforts to date have provided a number of useful carrot varieties with beneficial traits, there remains a great need in the art for new varieties with further improved traits. Such plants would benefit farmers and consumers alike by improving crop yields and/or quality. Some breeding objectives include varying the color, size and shape of the root, disease or pest resistance, yield, suitability to various climatic circumstances, and storage properties.

SUMMARY OF THE VARIOUS ASPECTS OF THE DISCLOSURE

The disclosure provides for a carrot variety NUN 89853 CAC, products thereof, and methods of using the same. NUN 89853 CAC is a red colored carrot variety and is suitable for the open field.

In an aspect, the disclosure provides a seed of carrot variety NUN 89853 CAC, wherein a representative sample of said seed has been deposited under Accession Number NCIMB 43441. The disclosure also provides for a plurality of seeds of NUN 89853 CAC. The carrot seed of NUN 89853 CAC may be provided as an essentially homogeneous population of carrot seed. The population of seed of NUN 89853 CAC may be particularly defined as being essentially free from other seed. The seed population may be grown into plants to provide an essentially homogenous population of carrot plants as described herein.

The disclosure also provides a plant grown from a seed of carrot variety NUN 89853 CAC and a plant part thereof. In another aspect, the disclosure provides for a hybrid carrot variety NUN 89853 CAC. The disclosure also provides for a progeny of carroty variety NUN 89853 CAC. In another aspect, the disclosure provides a plant or a progeny retaining all or all but one, two or three of the "distinguishing characteristics" or all or all but one, two or three of the "morphological and physiological characteristics" of carrot variety NUN 89853 CAC, and methods for producing that plant or progeny.

In an aspect, the disclosure provides a plant or a progeny having all the physiological and morphological characteristics of carrot variety NUN 89853 CAC when grown under the same environmental conditions. In another aspect, the plant or such progeny has all or all but one, two, or three of the physiological and morphological characteristics of carrot variety NUN 89853 CAC when measured under the same environmental conditions and e.g., evaluated at significance levels of 1%, 5% or (10% significance (which can also be expressed as p-value) for quantitative characteristics, wherein a representative sample of seed of carrot variety NUN 89853 CAC has been deposited under Accession Number NCIMB 43441. In another aspect, the plant or progeny has all or all but one or three of the physiological and morphological characteristics as listed in Tables 1 and 2 of carrot variety NUN 89853 CAC, when grown under the same environmental conditions and e.g., evaluated at significance levels of 1%, 5% or 10% significance (which can also be expressed as p-value) for quantitative characteristics.

In another aspect, a plant of carrot variety NUN 89853 CAC or progeny thereof has 18, 19, or more or all of the distinguishing characteristics as shown in Tables 1 and 2: 1) an average height of plant top; 2) an average diameter of plant top neck; 3) an average length of blade without petiole; 4) an average length of petiole from crown to $1^{st}$ leaf division; 5) an average diameter of petiole; 6) an average length of root minus taproot; 7) an average diameter of root at midpoint; 8) an average weight of root; 9) an average thickness of cortex (phloem); 10) an average thickness of core (xylem); 11) an average sugar content; 12) color of leaf blade; 13) petiole pubescence; 14) collar of root; 15) smoothness of the root surface; 16) presence of halo; 17) color of below ground root shoulder; 18) color of below ground root skin; 19) color of root cross section xylem; and 20) color of root cross section phloem.

In other aspects, the disclosure provides for a plant part obtained from carrot variety NUN 89853 CAC, wherein said plant part is: a root, or a part of a root, a harvested root, a root tip, a fruit, a part of a fruit, a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said varieties, hypocotyl, cotyledon, a pistil, an anther, and a flower or a part thereof. Roots are particularly important plant parts. In another aspect, the plant part obtained from carrot variety NUN 89853 CAC is a cell, optionally a cell in a cell or tissue culture. That cell may be grown into a plant of carrot variety NUN 89853 CAC.

The disclosure also provides a cell culture of carrot variety NUN 89853 CAC and a plant regenerated from carrot variety NUN 89853 CAC, which plant has all the characteristics of carrot variety NUN 89853 CAC, when grown under the same environmental conditions, as well as methods for culturing and regenerating carrot variety NUN 89853 CAC. Alternatively, a regenerated plant may have one characteristic that is different from carroty variety NUN 89853 CAC.

The disclosure further provides a vegetatively propagated plant of variety NUN 89853 CAC is provided having all or all but one, two or three of the morphological and physiological characteristics of carrot variety NUN 89853 CAC, when grown under the same environmental conditions.

The disclosure furthermore provides a carrot root produced on a plant grown from a seed of NUN 89853 CAC.

In another aspect, the disclosure provides a seed growing or grown on a plant of carrot variety NUN 89853 CAC (i.e., produced after pollination of the flower of carrot variety NUN 89853 CAC).

Definitions

"Carrot" refers herein to plants of the species *Daucus carota*. The most commonly eaten part of a carrot is the root.

"Cultivated carrot" refers to plants of *Daucus carota* (e.g., varieties, breeding lines or cultivars of the species *D. carota*, as well as crossbreds thereof, or crossbreds with other *Daucus carota* species), cultivated by humans and having good agronomic characteristics.

The terms "carrot plant designated NUN 89853 CAC", "NUN 89853 CAC", "NUN 89853" NUN 89853F1", "89853 CAC" or "carrot 89853" are used interchangeably herein and refer to a carrot plant of variety NUN 89853 CAC, representative seed has been deposited under Accession Number NCIMB 43441.

A "seed of NUN 89853 CAC" refers to a carrot seed which can be grown into a plant of carrot variety NUN 89853 CAC, wherein a representative sample of viable seed of carrot variety NUN 89853 CAC has been deposited under Accession Number NCIMB 43441. A seed can be in any stage of maturity, for example, a mature, viable seed, or an immature, non-viable seed. A seed comprises an embryo and maternal tissues.

An "embryo of NUN 89853 CAC" refers to an "F1 hybrid embryo" as present in a seed of carrot variety NUN 89853 CAC, a representative sample of said seed of carrot variety NUN 89853 CAC has been deposited under Accession Number NCIMB 43441.

A "seed grown on NUN 89853 CAC" refers to a seed grown on a mature plant of carrot variety NUN 89853 CAC or inside a fruit of NUN 89853 CAC. The "seed grown on NUN 89853 CAC" contains tissues and DNA of the maternal parent, NUN 89853 CAC. The "seed grown on NUN 89853 CAC" contains an F2 embryo. When said seed is planted, it grows into a first generation progeny plant of carrot variety NUN 89853 CAC.

An "essentially homogeneous population of carrot plants" is a population of plants where at least 97%, 98%, 99% or more of the total population of plants are plants of carrot variety NUN 89853 CAC.

The phrase "essentially free from other seed" refers to a population of seed where less than 3%, 2%, 1% or less of the total population of seed is seed that is not a carrot seed or, in another aspect, less than 3%, 2%, 1% or less of the total population of seed is seed that is not seed of carrot variety NUN 89853 CAC.

"Tissue culture" or "cell culture" refers to a composition comprising isolated cells of the same or a different type or a collection of such cells organized into parts of a plant. Tissue culture of various tissues of carrot and regeneration of plants therefrom is well known and widely published (see, e.g., Amholdt-Schmitt et al., 1995 Theor Appl Genet (1995) 91:809-815; Larkin and Scowcroft, (1981) Theor. Appl. Genet. 60, 197-214). Similarly, the methods of preparing cell cultures are known in the art.

"USDA descriptors" are the plant variety descriptors described for carrot in the "Objective description of Variety—Carrot (*Daucus carota*)," as published by U.S. Department of Agriculture, Agricultural Marketing Service, Science and Technology, Plant Variety Protection Office, Beltsville, Md. 20705 and which can be downloaded from the world-wide web at ams.usda.gov/ under services/plant-variety-protection/pvpo-c-forms under carrot. "Non-USDA descriptors" are other descriptors suitable for describing carrot.

"UPOV descriptors" are the plant variety descriptors described for carrot in the "Guidelines for the Conduct of Tests for Distinctness, Uniformity and Stability, TG/49/8 (Geneva 2007, last updated in 2015 Mar. 25), as published by UPOV (International Union for the Protection of New Varieties and Plants) and which can be downloaded from the world wide web at upov.int/ under edocs/tgdocs/en/tg049.pdf and is herein incorporated by reference in its entirety. Likewise, "UPOV methods" to determine specific parameters for the characterization of carrot are described at upov.int.

"RHS" refers to the Royal Horticultural Society (UK), which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007.

"Plant part" includes any part of a plant, such as a plant organ (e.g., harvested or non-harvested roots), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or a part of a plant (e.g., harvested tissues or organs), such as a root, or a part of a root, a harvested root, a root tip, a fruit, a harvested fruit, a part of a fruit, a leaf, a part of a leaf, pollen, an ovule, an embryo, a petiole, a shoot or a part thereof, a stem or a part thereof, a cutting, a seed, a part of a seed, seed coat or another maternal tissue, hypocotyl, cotyledon, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of carrot variety NUN 89853 CAC, and an embryo having one or two sets of chromosomes derived from the parent plant, e.g., from carrot variety NUN 89853 CAC. Such an embryo comprises two sets of chromosomes derived from carrot variety NUN 89853 CAC, if it produced from self-pollination of said variety, while an embryo derived from cross-fertilization of carrot variety NUN 89853 CAC will comprise only one set of chromosomes from said variety.

"Reference Variety" for NUN 89853 CAC refers herein to variety NUN 89849 CAC, a commercial variety from Nunhems B. V., with commercial name Rubyqueen, which has been planted in a trial together with carrot variety NUN 89853 CAC. Descriptors of carrot variety NUN 89853 CAC were compared to descriptors of variety NUN 89849 CAC.

"Harvest maturity" refers to the stage at which a carrot root is ready for harvest or the optimal time to harvest the root for the market, for processing or for consumption. In one aspect, harvest maturity is the stage suitable for producing baby carrots.

"Harvested plant material" refers herein to plant parts (e.g., roots removed from the soil in which they were growing) which have been collected for further storage and/or further use.

"Yield" means the total weight of all carrot roots harvested per hectare of a particular line or variety. It is understood that "yield" expressed as weight of all carrots harvested per hectare can be obtained by multiplying the number of plants per hectare times the "yield per plant".

"Marketable yield" means the total weight of all marketable carrot roots, especially roots that are not split, damaged or diseased, harvested per hectare of a particular line or variety.

"Refractometer % of soluble solids" refers to the percentage of soluble solids in juice of pureed roots (mainly sugar), as defined by the USDA. It is also expressed as ° Brix and indicates sweetness in the roots of carrot. Brix can be measured using a Brix meter (also known as Refractometer).

"Uniform throughout the root" refers to a characteristic such as color being identical throughout the entire plant part (e.g., throughout the root when it is cut in half).

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1 and 2 or "all or all but one, two or three of the physiological and morphological characteristics" of Tables 1 and 2.

The physiological and/or morphological characteristics mentioned above are commonly evaluated at significance levels of 1%, 5% or 10% if they are numerical (quantitative), or for having an identical degree (or type) if not numerical, if measured under the same environmental conditions. For example, a progeny plant or a Single Locus Converted plant or a mutated plant of carrot variety NUN 89853 CAC may have one or more (or all) of the essential physiological and/or morphological characteristics of said variety listed in Tables 1 and 2, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from the other carrot varieties, such as the Reference Variety (i.e., are different), when grown under the same environmental conditions. The distinguishing characteristics between carrot variety NUN 89853 CAC and the Reference Variety are described elsewhere herein and also can be seen in Tables 1 and 2. When comparing carrot variety NUN 89853 CAC to other varieties, the distinguishing characteristics may be different. In one aspect, the distinguishing characteristics may therefore include at least one, two, three or more (or all) of the characteristics listed in Tables 1 and 2. All numerical distinguishing characteristics are statistically significantly different at $p<0.05$ between carrot variety NUN 89853 CAC and the other variety (e.g., Reference Variety).

Carrot variety NUN 89853 CAC has the following distinguishing characteristics when compared to the Reference Variety as shown in Tables 1 and 2: 1) an average height of plant top; 2) an average diameter of plant top neck; 3) an average length of blade without petiole; 4) an average length of petiole from crown to $1^{st}$ leaf division; 5) an average diameter of petiole; 6) an average length of root minus taproot; 7) an average diameter of root at midpoint; 8) an average weight of root; 9) an average thickness of cortex (phloem); 10) an average thickness of core (xylem); 11) an average sugar content; 12) color of leaf blade; 13) petiole pubescence; 14) collar of root; 15) smoothness of the root surface; 16) presence of halo; 17) color of below ground root shoulder; 18) color of below ground root skin; 19) color of root cross section xylem; and 20) color of root cross section phloem, where the characteristics of carrot variety NUN 89853 CAC are compared to the characteristics of Reference Variety, when grown under the same environmental conditions.

Thus, a carrot plant "comprising the distinguishing characteristics of carrot variety NUN 89853 CAC" (such as a progeny plant) refers herein to a plant which does not differ significantly from said variety in the distinguishing characteristics above. Therefore, in one aspect, the disclosure provides a plant which does not differ significantly from carrot variety NUN 89853 CAC in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic is considered "the same" when the values have the same "degree" or "type" when scored using USDA and/or UPOV descriptors, if the plants are grown under the same environmental conditions.

As used herein, the term "variety", "cultivated carrot" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one carrot line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 89853 CAC. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another carrot plant of the same variety or another variety or (breeding) line, or with wild carrot plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration (optionally combined with transformation or mutation). Thus, a plant of carrot variety NUN 89853 CAC is the male parent, the female parent or both of a first generation progeny of carrot variety NUN 89853 CAC. Progeny may have all the physiological and morphological characteristics of variety NUN 89853 CAC when grown under the same environmental conditions. Using common breeding methods such as backcrossing or recurrent selection, mutation or transformation, one or more specific characteristics may be introduced into said variety, to provide a plant comprising all but 1, 2, or 3 or more of the morphological and physiological characteristics of carrot variety NUN 89853 CAC.

The terms "gene converted" or "conversion plant" or "single locus converted plant" in this context refer to carrot plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent transferred into the parent via e.g., the backcrossing technique (optionally including reverse breeding or reverse synthesis of breeding lines). It is understood that only the addition of a further characteristics (e.g., addition of gene conferring a further characteristic, such as a disease resistance gene), but also the replacement/modification of an existing characteristics by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a carrot variety are recovered in addition to the characteristics of the single locus having been transferred into the variety via the backcrossing technique, or wherein the morphological and physiological characteristic of the variety has been replaced/modified in the variety. In case of a hybrid, the gene may be introduced in the male or female parental line.

"Average" refers herein to the arithmetic mean.

The term "mean" refers to the arithmetic mean of several measurements. The skilled person understands that the appearance of a plant depends to some extent on the growing conditions of said plant. Thus, the skilled person understands suitable growing conditions for carrot variety NUN 89853 CAC. The mean, if not indicated otherwise within this application, refers to the arithmetic mean of measurements on at least 10 different, randomly selected plants of a variety or line.

DETAILED DESCRIPTION OF VARIOUS ASPECTS OF THE DISCLOSURE

The disclosure relates to a plant of carrot variety NUN 89853 CAC, wherein a representative sample of seeds of said carrot variety has been deposited under Budapest Treaty, with Accession number NCIMB 43441. NUN 89853 CAC is a red colored carrot variety and is suitable for the open field.

The disclosure relates to a seed of carrot variety NUN 89853 CAC, wherein a representative sample of said seed has been deposited under Budapest Treaty with Accession number NCIMB 43441.

In another aspect, the disclosure provides for a carrot plant part of variety NUN 89853 CAC, preferably a root, a representative sample of seed from said variety has been deposited under Budapest Treaty, with Accession number NCIMB 43441.

A seed of hybrid carrot variety NUN 89853 CAC is obtainable by crossing the male parent of carrot variety NUN 89853 CAC with the female parent of carrot variety NUN 89853 CAC and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of carrot variety NUN 89853 CAC.

Also provided is a plant of carrot variety NUN 89853 CAC, or a root or other plant part thereof, produced from a seed, wherein a representative sample of said seed has been deposited under Budapest Treaty, with Accession Number NCIMB 43441.

Also provided is a plant part obtained from carrot variety NUN 89853 CAC, wherein said plant part is: a root, or a part of a root, a harvested root, a root tip, a fruit, a harvested fruit, a part of a fruit, a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said varieties, hypocotyl, cotyledon, a pistil, an anther, and a flower or a part thereof. Roots are particularly important plant parts. In a further aspect, the plant part obtained from carrot variety NUN 89853 CAC is a cell, optionally a cell in a cell or tissue culture. That cell may be grown into a plant of carrot variety NUN 89853 CAC. A part of carrot variety NUN 89853 CAC (or of progeny of that variety or of a plant having all physiological and/or morphological characteristics but one, two or three which are different from those of carrot variety NUN 89853 CAC) further encompasses any cells, tissues, organs obtainable from the seedlings or plants in any stage of maturity.

The disclosure also provides for a food or feed product or a processed product comprising or consisting of a plant part described herein, wherein the plant part can be identified as a part of the plant described herein. Preferably, the plant part is a carrot root or part thereof and/or an extract from a root or another plant part described herein comprising at least one cell of carrot variety NUN 89853 CAC. The food or feed product may be fresh or processed, e.g., dried, grinded, powdered, pickled, chopped, cooked, roasted, in a sauce, in a sandwich, pasted, pureed or concentrated, juiced, pickled, canned, steamed, boiled, fried, blanched and/or frozen, baby-carrots etc.

Such a plant part of carrot variety NUN 89853 CAC can be stored and/or processed further. The disclosure also provides for a food or feed products comprising one or more of such parts, such as canned, chopped, cooked, roasted, in a sauce, in a sandwich, pasted, pureed or concentrated, juiced, frozen, dried, pickled, or powdered carrot root from carrot variety NUN 89853 CAC or from progeny of said variety, or from a derived variety, such as a plant having all but one, two or three physiological and/or morphological characteristics of carrot variety NUN 89853 CAC.

In another aspect, the disclosure provides for a carrot root of variety NUN 89853 CAC, or a part of a root of said variety. The root can be in any stage of maturity, for example, immature or mature. In another aspect, the disclosure provides for a container comprising or consisting of a plurality of harvested carrot roots or parts of roots of said variety, or roots of progeny thereof, or roots of a derived variety.

In another aspect, the plant, plant part or seed of carrot variety NUN 89853 CAC is inside one or more containers. For example, the disclosure provides containers such as cans, boxes, crates, bags, cartons, Modified Atmosphere Packaging, films (e.g., biodegradable films), etc. comprising a plant or a part of a plant (fresh and/or processed) or a seed of carrot variety NUN 89853 CAC. In a particular aspect, the container comprises a plurality of seeds of carrot variety NUN 89853 CAC, or a plurality of plant parts of carrot variety NUN 89853 CAC.

The disclosure further relates to a carrot variety NUN 89853 CAC, which when compared to its Reference Variety has the following distinguishing characteristics as shown in Tables 1 and 2: 1) an average height of plant top; 2) an average diameter of plant top neck; 3) an average length of blade without petiole; 4) an average length of petiole from crown to $1^{st}$ leaf division; 5) an average diameter of petiole; 6) an average length of root minus taproot; 7) an average diameter of root at midpoint; 8) an average weight of root; 9) an average thickness of cortex (phloem); 10) an average thickness of core (xylem); 11) an average sugar content; 12) color of leaf blade; 13) petiole pubescence; 14) collar of root; 15) smoothness of the root surface; 16) presence of halo; 17) color of below ground root shoulder; 18) color of below ground root skin; 19) color of root cross section xylem; and 20) color of root cross section phloem, where the characteristics are determined at the 5% significance level for plants grown under the same environmental conditions. Also encompassed are parts of that plant.

In one aspect, a plant of carrot variety NUN 89853 CAC or a progeny plant thereof, comprises all of the following morphological and/or physiological characteristics (i.e., average values of distinguishing characteristics, as indicated on the USDA Objective description of variety—carrot (unless indicated otherwise)) as shown in Tables 1 and 2: 1) an average height of plant top; 2) an average diameter of plant top neck; 3) an average length of blade without petiole; 4) an average length of petiole from crown to $1^{st}$ leaf division; 5) an average diameter of petiole; 6) an average length of root minus taproot; 7) an average diameter of root at midpoint; 8) an average weight of root; 9) an average thickness of cortex (phloem); 10) an average thickness of core (xylem); 11) an average sugar content; 12) color of leaf blade; 13) petiole pubescence; 14) collar of root; 15) smoothness of the root surface; 16) presence of halo; 17) color of below ground root shoulder; 18) color of below ground root skin; 19) color of root cross section xylem; and 20) color of root cross section phloem, where the characteristics are determined at the 5% significance level for plants grown under the same environmental conditions. An example of values for the distinguishing characteristics collected in a trial can be found in Tables 1 and 2. A part of this plant is provided.

The disclosure further provides a carrot plant which does not differ from the physiological and morphological characteristics of the plant of carrot variety NUN 89853 CAC as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a root or a part thereof.

The disclosure also provides a tissue or cell culture comprising cells of carrot variety NUN 89853 CAC. Such a tissue culture can, for example, be grown on plates or in liquid culture, or be frozen for long term storage. The cells of carrot variety NUN 89853 CAC used to start the culture can be selected from any plant part suitable for vegetative reproduction, or in a particular aspect can be selected from an embryo, a meristem, a cotyledon, a hypocotyl, pollen, a leaf, an anther, a root, a root tip, a pistil, a petiole, a flower, a fruit, a seed, a stem and a stalk. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a carrot plant regenerated from the tissue or cell culture of carrot variety NUN 89853 CAC, wherein the regenerated plant is not significantly different from carrot variety NUN 89853 CAC in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a carrot plant regenerated from the tissue or cell culture of carrot variety NUN 89853 CAC, wherein the plant has all of the physiological and morphological characteristics of said variety determined (e.g., at the 5% significance level) when grown under the same environmental conditions. Similarity or difference of a characteristic is determined by measuring the characteristics of a representative number of plants grown under the same environmental conditions, determining whether type/degree characteristics are the same or different and determining whether numerical characteristics are different at the 5% significance level.

Carrot variety NUN 89853 CAC, or its progeny, or a plant having all morphological and/or physiological characteristics but one, two or three which are different from those of carrot variety NUN 89853 CAC, can also be reproduced using vegetative reproduction methods. Therefore, the disclosure provides for a method of producing a plant, or a plant part of carrot variety NUN 89853 CAC, comprising vegetative propagation of said variety. Vegetative propagation comprises regenerating a whole plant from a plant part of carrot variety NUN 89853 CAC or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of carrot variety NUN 89853 CAC. In certain aspects, the method comprises: (a) collecting tissue or cells capable of being propagated from carrot variety NUN 89853 CAC to obtain proliferated shoots; (b) rooting said proliferated shoots to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from said part of carrot variety NUN 89853 CAC. In a particular aspect, the part of the plant to be propagated is a cutting, a cell culture or a tissue culture.

The disclosure also provides for a vegetatively propagated plant of carrot variety NUN 89853 CAC (or from progeny of said variety or from or a plant having all but one, two or three physiological and/or morphological characteristics of carrot variety NUN 89853 CAC) wherein the plant has all of the morphological and physiological characteristics of carrot variety NUN 89853 CAC, when the characteristics are determined at the 5% significance level for plants grown under the same conditions. In another aspect, the propagated plant has all but one, two or three of the morphological and physiological characteristics of carrot variety NUN 89853 CAC, when the characteristics are determined at the 5% significance level for plants grown under the same conditions. A part of said propagated plant or said propagated plant with one, two or three differences is also provided.

In another aspect, the disclosure provides a method for producing a carrot plant part, such as a root, comprising growing a plant of carrot variety NUN 89853 CAC until it develops a root, and collecting the root. Preferably, the root is collected at harvest maturity. In another aspect, the root is collected at baby stage. A plant of carrot variety NUN 89853 CAC can be produced by seeding directly in the soil (e.g., field) (see, e.g., https://anrcatalog.ucanr.edu/pdf/7226.pdf).

In still another aspect, the disclosure provides a method of producing a carrot plant, comprising crossing a plant of carrot variety NUN 89853 CAC with a second carrot plant at least once, allowing seed to develop and optionally harvesting said respective progeny seed. The skilled person can select progeny from said crossings. Optionally, the respective progeny is crossed twice, thrice, or four, five, six or seven times, and allowed to set seed. In another aspect, the first step in "crossing" comprises planting seeds of a first and a second parent carrot plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect, the disclosure provides a method of producing a plant, comprising selfing a plant of carrot variety NUN 89853 CAC one or more times, and selecting a progeny plant from said selfing. In one aspect, the progeny plant retains all the distinguishing characteristics of carrot variety NUN 89853 CAC described above, when grown under the same environmental conditions. In a different aspect, the progeny plant, comprises all (or all but one, two or three) of the physiological and morphological characteristic of carrot variety NUN 89853 CAC as listed in Tables 1 and 2.

In other aspects, the disclosure provides a progeny plant of carrot variety NUN 89853 CAC, such as a progeny plant obtained by further breeding that variety. Further breeding with carrot variety NUN 89853 CAC, includes selfing that variety and/or cross-pollinating that variety with another carrot plant or variety one or more times. In a particular aspect, the disclosure provides for a progeny plant that retains all or all but one, two, or three of the morphological and physiological characteristics of carrot variety NUN 89853 CAC, optionally all or all but one, two, or three characteristics as listed in Tables 1 and 2, determined at the 5% significance level for numerical characteristics, when grown under the same environmental conditions. In another aspect, the progeny is a first generation progeny, i.e., the ovule or the pollen (or both) used in the crossing is an ovule or pollen of carrot variety NUN 89853 CAC, i.e., the pollen comes from an anther of carrot variety NUN 89853 CAC and the ovule comes from an ovary of carrot variety NUN 89853 CAC. In another aspect, the disclosure provides for a vegetative reproduction of the variety and a plant having all, or all but one, two, or three of the physiological and morphological characteristics of carrot variety NUN 89853 CAC (e.g., as listed in Tables 1 and 2).

The disclosure also provides a method for collecting pollen of carrot variety NUN 89853 CAC, comprising collecting the pollen from a plant of carrot variety NUN 89853 CAC. Alternatively, the method comprises growing a plant of carrot variety NUN 89853 CAC until at least one flower contains pollen and collecting the pollen. In a particular aspect, the pollen is collected when it is mature or ripe. A suitable method for collecting pollen comprises collecting anthers or the part of the anther that contains pollen, for example, by cutting it off. Pollen can be collected in containers. Optionally, collected pollen can be used to pollinate a carrot flower.

The morphological and/or physiological differences between two different individual plants described herein (e.g., between carrot NUN 89853 CAC and a progeny of said carrot variety) or between a plant of carrot variety NUN 89853 CAC or progeny of said variety, or a plant having all, or all but 1, 2, or 3 of the physiological and morphological characteristics of carrot variety NUN 89853 CAC and another known variety can easily be established by growing said variety next to each other or next to the other variety (in the same field, under the same environmental conditions (in the same field, optionally, next to each other), preferably in repeated several locations which are suitable for cultivation of carrots, and measuring morphological and/or physiological characteristics of a representative number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example maturity, days from seeding to harvest, plant habit, leaf color, petiole anthocyanin, root shape, root collar, root halo, root shoulder, number of secondary root scars, disease resistance, insect resistance, can be measured and directly compared for species of carrot. Thus, the disclosure comprises carrot plant having one, two or three physiological and/or morphological characteristics which are different from those of the plant of carrot variety NUN 89853 CAC and which otherwise has all the physiological and morphological characteristics of the plant of carrot variety NUN 89853 CAC, when determined at the 5% significance level for plants grown under the same environmental conditions. In another aspect, the different characteristic is affected by a mutation, optionally induced mutation, or by transformation.

The morphological and physiological characteristics of carrot variety NUN 89853 CAC are provided, for example, in Tables 1 and 2, as collected in a trial according to USDA and/or UPOV standards. Encompassed herein is also a plant obtainable from carrot variety NUN 89853 CAC (e.g., by selfing and/or crossing and/or backcrossing with said variety and/or progeny of said variety) comprising all or all but one, two or three of the physiological and morphological characteristics of carrot variety NUN 89853 CAC listed in Tables 1 and 2 (as determined at the 5% significance level for numerical characteristics or identical for non-numerical characteristics) when grown under the same environmental conditions and/or comprising one or more (or all; or all except one, two or three) characteristics when grown under the same environmental conditions. The morphological and/or physiological characteristics may vary somewhat with variation in the environment (such as temperature, light intensity, day length, humidity, soil, fertilizer use, disease vectors), which is why a comparison under the same environmental conditions is preferred. Colors can best be measured using Royal Horticultural Society (RHS) Chart.

Also, at-harvest and/or post-harvest characteristics of roots can be compared, such as by cold storage holding quality (browning), post-harvest rind firmness and/or flesh firmness, and juiciness can be measured using known methods.

The disclosure also provides for a method of producing a new carrot plant. The method comprises crossing a plant of carrot variety NUN 89853 CAC, or a plant comprising all but 1, 2, or 3 of the morphological and physiological characteristics of said variety (as listed in Tables 1 and 2), or a progeny plant thereof, either as male or as female parent, with a second carrot plant (or a wild relative of carrot) one or more times, and/or selfing a carrot plant of variety NUN 89853 CAC, or a progeny plant thereof, one or more times, and selecting progeny from said crossing and/or selfing. The second carrot plant may, for example, be a line or variety of the species *Daucus carota*, or other *Daucus* species or even other Apiaceae species.

The disclosure provides for methods of producing plants which retain all the morphological and physiological characteristics of a plant described herein. The disclosure provides also for methods of producing a plant comprising all but 1, 2, or 3 or more of the morphological and physiological characteristics of carrot variety NUN 89853 CAC (e.g., as listed in Tables 1 and 2), but which are still genetically closely related to said carrot variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to carrot variety NUN 89853 CAC if its DNA fingerprint is at least 80%, 90%, 95% or 98% identical to the fingerprint of carrot variety NUN 89853 CAC. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Shim and Jorgensen, Theor Appl Genet (2000) 101:227-233). The disclosure also provides a plant and a variety obtained or selected by applying these methods on carrot variety NUN 89853 CAC. Such a plant may be produced by traditional breeding techniques or mutation or transformation or in another aspect, a plant may simply be identified and selected amongst plants of said variety, or progeny of said variety, e.g., by identifying a variant within carrot variety NUN 89853 CAC, which variant differs from the variety described herein in one, two, or three of the morphological and/or physiological characteristics (e.g., characteristics listed in Tables 1 and 2). In one aspect, the disclosure provides a plant of carrot variety NUN 89853 CAC having a Jaccard's Similarity index with said variety of at least 0.8, e.g., at least 0.85, 0.9, 0.95, 0.98 or even at least 0.99.

In some aspect, the disclosure provides a carrot plant comprising genomic DNA having at least 95%, 96%, 9, 98%, or 99% sequence identity compared to the genomic DNA sequence of a plant of carrot variety NUN 89853 CAC, as deposited under Accession Number NCIMB 43441. In some aspects, the carrot plant further comprises all or all but 1, 2, or 3 of the morphological and physiological characteristics of carrot variety NUN 89853 CAC (e.g., as listed in Tables 1 and 2). In other aspects, the carrot plant is a hybrid derived from a seed or plant of carrot variety NUN 89853 CAC.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

The disclosure also provides methods for determining the identity of parental lines described herein, in particular the identity of the female line. US2015/0126380, which is incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant carrot variety NUN 89853 CAC, or is a progeny of said variety, because the seed coat of the seed is a maternal tissue genetically identical to carrot variety NUN 89853 CAC. In one aspect, the disclosure relates to a carrot seed coat comprising maternal tissue of carrot NUN 89853 CAC. In another particular aspect, the disclosure provides a method of identifying the female parental line of carrot variety NUN 89853 CAC by analyzing the seed coat or another maternal tissue of said seed.

By crossing and/or selfing also (one or more) single traits may be introduced into the carrot variety NUN 89853 CAC (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 89853 CAC by breeding with said variety.

Any pest or disease resistance genes may be introduced into carrot variety NUN 89853 CAC, progeny of said variety or into a plant comprising all but 1, 2, or 3 or more of the morphological and physiological characteristics of carrot variety NUN 89853 CAC (e.g., as listed in Tables 1 and 2). Resistance to one or more of the following diseases or pests may be introduced into plants described herein: *Alternaria* Leaf Blight (*Alternaria dauci*), Aster Yellows (*Macrosteles fascifrons*), Cavity Spot (*Pythium sulcatum* and *P. violae*), Cercospora Blight or Carrot Early Blight (*Cerocospora carotae*), Bacterial Blight (*Xanthomonas* carotae), Powdery Mildew (*Erysiphe heraclei*), Phytium Root Dieback (*Pythium* spp.), Sclerotinia Decay or Watery Soft Rot (*Sclerotinia* spp.), Cottony Soft Rot (*Sclerotinia sclerotiorum*), Southern Blight (*Sclerotium rolfsii*), Bacterial Soft Rot (*Erwinia carotovora*), Black Root Rot (*Alternaria radicina*), Gray Mold (*Botrytis* spp.), Sour Rot (*Geothrichurn* spp.), Root Knot Nematode (*Meloidogyne* spp.), Stubby Root Nematode (*Trichodorus* spp., and *Paratrichodorus* spp.), Needle Nematode (*Longidorus africanus*), Nutsedges Yellow (*Cyperus esculentus*), Nutsedges Purple (*C. rotundus*), Saltmarsh Catterpillars (*Estigmene acrea*), Cotton-melon Aphid (*Aphis gossypii*), and/or Silverleaf Whitefly (*Bemisia argentifolii*). Other resistances, against pathogenic viruses (e.g., Motley Dwarf Virus, Carrot Thin Leaf Virus), fungi, bacteria, nematodes, insects or other pests may also be introduced.

The disclosure also provides a method for developing a carrot plant in a carrot breeding program, using a carrot plant of variety NUN 89853 CAC, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing carrot variety NUN 89853 CAC or progeny of said variety, or a plant comprising all but 1, 2, or 3 or more of the morphological and physiological characteristics of carrot variety NUN 89853 CAC (e.g., as listed in Tables 1 and 2), with a different carrot plant, and wherein one or more offspring of the crossing are subject to one or more plant breeding techniques: recurrent selection, backcrossing, pedigree breeding, mass selection, mutation breeding and genetic marker enhanced selection (see, e.g., Stein and Nothnagel, (1995) Plant Breeding 114, 1-11). For breeding methods in general, see, e.g., Principles of Plant Genetics and Breeding, 2007, George Acquaah, Blackwell Publishing, ISBN-13: 978-1-4051-3646-4.

The disclosure also provides a carrot plant comprising at least a first set of the chromosomes of carrot variety NUN 89853 CAC, a sample of seed of said carrot variety has been deposited under Accession Number NCIMB 43441; optionally further comprising a single locus conversion, wherein said plant has essentially all of the morphological and physiological characteristics of the plant comprising at least a first set of the chromosomes of said variety. In another aspect, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one aspect, a plant of carrot variety NUN 89853 CAC may also be mutated (by e.g., irradiation, chemical mutagenesis, heat treatment, etc.) and mutated seeds or plants may be selected in order to change one or more characteristics of said variety. Methods such as TILLING may be applied to carrot populations in order to identify mutants. Similarly, carrot variety NUN 89853 CAC may be transformed and regenerated, whereby one or more chimeric genes are introduced into the variety or into a plant comprising all but 1, 2, 3, or more of the morphological and physiological characteristics (e.g., as listed in Tables 1 and 2). Transformation can be carried out using standard methods, such as *Agrobacterium tumefaciens* mediated transformation or biolistics, followed by selection of the transformed cells and regeneration into plants. A desired trait (e.g., genes conferring pest or disease resistance, herbicide, fungicide or insecticide tolerance, etc.) can be introduced into carrot variety NUN 89853 CAC, or progeny of said variety, by transforming said variety or progeny of said variety with a transgene that confers the desired trait, wherein the transformed plant retains all or all but one, two or three of the physiological and/or morphological and/or physiological characteristics of carrot variety NUN 89853 CAC or the progeny of said variety and contains the desired trait. In another aspect, the transformation or mutation confers a trait wherein the trait is yield, storage properties, color, male sterility, herbicide tolerance, insect resistance, pest resistance, disease resistance, environmental stress tolerance, modified carbohydrate metabolism and modified protein metabolism.

The disclosure provides a method of producing a carrot plant having a desired trait, comprising mutating a plant of carrot variety NUN 89853 CAC or a cell thereof and selecting a plant with the desired trait, wherein the mutated plant retains all or all but one of the physiological and morphological characteristics of said carrot variety, optionally as described in Tables 1 and 2, and contains the desired trait and wherein a representative sample of seed of carrot variety NUN 89853 CAC has been deposited under Accession Number NCIMB 43441. In another further aspect, the desired trait is yield, high anthocyanin, root size and shape, storage properties, color, male sterility, herbicide tolerance, insect resistance, pest resistance, disease resistance, environmental stress tolerance, modified carbohydrate metabolism, modified protein metabolism, and ripening.

A suitable method for inducing mutation in carrot variety NUN 89853 CAC comprises the steps of:
  a. exposing the seed, the plant or the plant part of the cell of carrot variety NUN 89853 CAC to a mutagenic compound or to radiation, wherein a representative sample of seed of carrot variety NUN 89853 CAC is deposited under Accession Number NCIMB 43441;
  b. selecting the seed, the plant or plant part or the cell of carrot variety NUN 89853 CAC having a mutation; and
  c. optionally growing and/or multiplying the seed, plant or plant part or cell of NUN 89853 CAC having the mutation.

The disclosure also provides a plant having one, two or three physiological and/or morphological characteristics which are different from those of carrot variety NUN 89853 CAC and which otherwise has all the physiological and morphological characteristics of said carrot variety, wherein a representative sample of seed of carrot variety NUN 89853 CAC has been deposited under Accession Number NCIMB 43441. In particular, variants which differ from carrot variety NUN 89853 CAC in none, one, two or three of the characteristics mentioned in Tables 1 and 2 are encompassed.

A part of carrot variety NUN 89853 CAC (or of progeny of said variety or of a plant having all physiological and/or morphological characteristics but one, two or three which are different from those of said variety) encompasses any cells, tissues, organs obtainable from the seedlings or plants, such as but not limited to: a carrot root or a part thereof, a cutting, hypocotyl, cotyledon, seed coat, pollen and the like. Such parts can be stored and/or processed further. Encompassed are therefore also food or feed products comprising a part of carrot variety NUN 89853 CAC or a part of progeny of said variety, or a part of a plant having all but one, two or three physiological and/or morphological characteristics of carrot variety NUN 89853 CAC, comprising one or more of such parts, optionally processed (such as canned, chopped, cooked, roasted, in a sauce, in a sandwich, pasted, pureed or concentrated, juiced, frozen, dried, pickled, or powdered).

In one aspect, the disclosure provides a haploid plant and/or a doubled haploid plant of carrot variety NUN 89853 CAC, or of a plant having all but one, two or three physiological and/or morphological characteristics of carrot variety NUN 89853 CAC, or progeny of said carrot variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with chromosome doubling agent and regenerating the cells or tissues into a whole plant.

In another aspect, the disclosure comprises method for making double haploid cells from haploid cells of carrot variety NUN 89853 CAC, comprising doubling cells of carrot variety NUN 89853 CAC with a chromosome doubling agent such as colchicine treatment (see, e.g., Nikolova and Niemirowicz-Szczytt (1996) Acta Soc Bot Pol 65:311-317).

In another aspect, the disclosure provides haploid plants and/or doubled haploid plants derived from carrot variety NUN 89853 CAC that, when combined, make a set of parents of carrot variety NUN 89853 CAC. The haploid plant and/or the doubled haploid plant of carrot variety NUN 89853 CAC can be used in a method for generating parental lines of carrot variety NUN 89853 CAC.

Using methods known in the art like "reverse synthesis of breeding lines" or "reverse breeding," it is possible to produce parental lines for a hybrid plant such as carrot variety NUN 89853 CAC. A skilled person can take any individual heterozygous plant (called a "phenotypically superior plant" in Example 2 of US2015/0245570; which is hereby incorporated by reference in its entirety; carrot variety NUN 89853 CAC is such a plant) and generate a combination of parental lines (reverse breeding parental lines) that, when crossed, produce the variety NUN 89853 CAC. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., carrot variety NUN 89853 CAC), comprises in one aspect: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for a hybrid organism.

In another aspect, the method for producing parental lines for hybrid organisms, e.g., of carrot variety NUN 89853 CAC, which when crossed reconstitute the genome of carrot variety NUN 89853 CAC, comprising:
  a. defining a set genetic markers that are present a heterozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous forms (B vs. A, or A vs. B); and
  d. optionally repeating steps b) and c) until at least one pair of progeny organisms that have complementary alleles for at least a subset of the genetic markers had been selected as parental lines for a hybrid.

The disclosure relates to a method of producing a combination of parental lines of a plant of carrot variety NUN 89853 CAC, comprising the step of making doubled haploid cells from haploid cells from said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of carrot variety NUN 89853 CAC when these parental lines are crossed. In still another aspect, the disclosure relates to a combination of parental lines from which a seed or plant having all physiological and/or morphological characteristics of carrot variety NUN 89853 CAC (when the characteristics are determined at the 5% significance level for plants grown under the same conditions).

In another aspect, the disclosure provides a method of introducing a single locus conversion or single trait conversion or a desired trait into carrot variety NUN 89853 CAC comprising:
  a. obtaining a combination of a parental lines of carrot variety NUN 89853 CAC, optionally through reverse synthesis of breeding lines;
  b. introducing a single locus conversion in at least one of the parents of step a; and
  c. crossing the converted parent with the other parent of step a to obtain seed of carrot variety NUN 89853 CAC.

A combination of a male and a female parental line of carrot variety NUN 89853 CAC can be generated by methods described herein, for example, through reverse synthesis of breeding lines.

In another aspect, the disclosure provides a method of introducing a single locus conversion or single trait conversion or a desired trait into carrot variety NUN 89853 CAC, comprising introducing a single locus conversion in at least one of the parents of carrot variety NUN 89853 CAC, and crossing the converted parent with the other parent of carrot variety NUN 89853 CAC to obtain seed of said carrot variety.

In another aspect, introducing a single locus conversion in at least one of the parents comprise:
  a. obtaining a cell or tissue culture of cells of the parental line of carrot variety NUN 89853 CAC;
  b. genetically transforming or mutating said cells;
  c. growing the cells into a plant; and
  d. optionally selecting plants that contain the single locus conversion, the single trait conversion or the desired trait.

In another method, the step of introducing a single locus conversion in at least one of the parent plants comprises:
  a. crossing the parental line of carrot variety NUN 89853 CAC with a second carrot plant comprising the single locus conversion, the single trait conversion or the desired trait;
  b. selecting Flprogeny plants that contain the single locus conversion, the single trait conversion or the desired trait;
  c. crossing said selected progeny plants of step ii with the parental line of step i, to produce a backcross progeny plant;
  d. selecting backcross progeny plants comprising the single locus conversion, the single trait conversion or the desired trait and otherwise all or all but one, two or three of the morphological and physiological characteristics the parental line of step i to produce selected backcross progeny plants; and
  e. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions. The disclosure further relates to plants obtained by this method.

In any of the above methods, wherein the single locus conversion concerns a trait, the trait may be yield or pest resistance or disease resistance. In one aspect, the trait is disease resistance and the resistance is conferred to Alternaria Leaf Blight (*Alternaria dauci*), Aster Yellows (*Macrosteles fascifrons*), Cavity Spot (*Pythium sulcatum* and *P. violae*), Cercospora Blight or Carrot Early Blight (*Cerocospora carotae*), Bacterial Blight (*Xanthomonas carotae*), Powdery Mildew (*Erysiphe heraclei*), Phytium Root Dieback (*Pythium* spp.), Sclerotinia Decay or Watery Soft Rot (*Sclerotinia* spp.), Cottony Soft Rot (*Sclerotinia sclerotiorum*), Southern Blight (*Sclerotium rolfsii*), Bacterial Soft Rot (*Erwinia carotovora*), Black Root Rot (*Alternaria radicina*), Gray Mold (*Botrytis* spp.), Sour Rot (*Geothrichurn* spp.), Root Knot Nematode (*Meloidogyne* spp.), Stubby Root Nematode (*Trichodorus* spp., and *Paratrichodorus* spp.), Needle Nematode (*Longidorus africanus*), Nutsedges Yellow (*Cyperus esculentus*), Nutsedges Purple (*C. rotundus*), Saltmarsh Catterpillars (*Estigmene acrea*), Cotton-melon Aphid (*Aphis gossypii*), and/or Silverleaf Whitefly (*Bemisia argentifolii*). Other resistances, against pathogenic viruses (e.g., Motley Dwarf Virus, Carrot Thin Leaf Virus), fungi, bacteria, nematodes, insects or other pests may also be introduced.

The disclosure also provides a combination of parental lines which, when crossed, produce a seed or plant having all physiological and/or morphological characteristics of carrot variety NUN 89853 CAC but one, two or three which are different (when grown under the same environmental conditions), as well as a seed or plant having all physiological and/or morphological characteristics of carrot variety NUN 89853 CAC but one, two or three which are different (when the characteristics are determined at the 5% significance level for plants grown under the same conditions).

Also provided is a plant part obtainable from carrot variety NUN 89853 CAC or from progeny of said variety or from a plant having all but one, two or three physiological and/or morphological characteristics which are different from those of carrot variety NUN 89853 CAC, or from a vegetatively propagated plant of carrot variety NUN 89853 CAC (or from its progeny or from a plant having all or all but one, two or three physiological and/or morphological characteristics which are different from those of carrot variety NUN 89853 CAC), wherein said plant part is a root, or a part of a root, a harvested root, a root tip, a fruit, a harvested fruit, a part of a fruit, a leaf, a part of a leaf, pollen, an ovule, a cell, a petiole, a shoot or a part thereof, a stem or a part thereof, a cutting, a seed, a part of a seed, seed-coat or another maternal tissue which is part of a seed grown on NUN 89853 CAC, or hypocotyl, cotyledon, a pistil, an anther, or a flower or a part thereof.

In another aspect, the disclosure provides a method of determining the genotype of a plant of the disclosure comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

The disclosure further provides for a food or feed product comprising or consisting a plant part of carrot variety NUN 89853 CAC or a part of progeny of said carrot variety, or a part of a plant having all but one, two, or three of the physiological and/or morphological characteristics of carrot variety NUN 89853 CAC, comprising one or more such parts, optionally processed (such as canned, chopped, cooked, roasted, in a sauce, in a sandwich, pasted, pureed or concentrated, juiced, frozen, dried, pickled, or powdered).

All documents (e.g., patent publications) are herein incorporated by reference in their entirety, including the following cited references:

UPOV, "Guidelines for the Conduct of Tests for Distinctness, Uniformity and Stability, TG/49/8 (Geneva 2007, last updated in 2015-03-25), world-wide web at upov.int under edocs/tgdocs/en/tg049.pdf.

US Department of Agriculture, Agricultural Marketing Service, "Objective description of Variety—Carrot (*Daucus carota*)," world wide web at ams.usda.gov/services/plant-variety-protection/pvpo-c-forms, under carrot.

Acquaah, G., "Principles of Plant Genetics and Breeding", Blackwell Publishing, 2007, ISBN-13: 978-1-4051-3646-4.

Arnhold-Schmitt, B., et. al., "Physiological Aspects of Genome Variability in Tissue Culture. I. Growth Phase-Dependent Differential DNA Methylation of the Carrot Genome (*Daucus carota* L.) During Primary Culture", Theoretical and Applied Genetics, 1995, vol. 91, no. 5, pp. 809-815

Jhang, T., et. al., "Efficiency of Different Marker Systems for Molecular Characterization of Subtropical Carrot Germplasm," The Journal of Agricultural Science, 2010, vol. 148, no. 2, pp. 171-181.

Larkin, P. J., et. al., "Somaclonal Variation—A Novel Source of Variability from Cell Cultures for Plant Improvement", Theoretical and Applied Genetics, 1981, vol. 60, no. 4, pp. 197-214.

Martin, E., et al., "Identification of Markers Linked to Agronomic Traits in Globe Artichoke", Australian Journal of Crop Science, 2008, vol. 1(2), pp. 43-46.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Rice, P., et al., "EMBOSS: The European Molecular Biology Open Software Suite", Trends in Genetics, 2000, vol. 16, Issue 6. pp. 276-277.

Shim, S. J., and Jorgensen, R. B., "Genetic Structure in Cultivated and Wild Carrots (*Daucus carota* L.) Revealed by AFLP Analysis", Theor Appl Genet, 2000, vol. 101, pp. 227-233.

Stein, M., et. al., "Some Remarks on Carrot Breeding (*Daucus carota saativus* Hoffm.), Plant Breeding, 1995, vol. 114, no. 1, pp. 1-11.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

US2015/0126380

US2015/0245570

Development of NUN 89853 CAC

The hybrid carrot variety NUN 89853 CAC was developed from a male and female proprietary inbred line of Nunhems. The female and male parents were crossed to produce hybrid (F1) seeds of carrot variety NUN 89853 CAC. The seeds of carrot variety NUN 89853 CAC can be grown to produce hybrid plants and parts thereof (e.g., carrot roots). The hybrid carrot variety NUN 89853 CAC can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that carrot variety NUN 89853 CAC is uniform and stable.

Deposit Information

A total of 2500 seeds of the hybrid carrot variety NUN 89853 CAC has been deposited according to the Budapest Treaty by Nunhems B.V. on Jun. 18, 2019, at the NCIMB Ltd., Ferguson Building, Craibstone Estate, Bucksburn, Aberdeen AB21 9YA, United Kingdom (NCIMB). The deposit has been assigned NCIMB number 43441. A deposit of carrot variety NUN 89853 CAC and the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq.).

The most similar variety to carrot variety NUN 89853 CAC is a variety from Nunhems B.V. with the commercial name Rubyqueen.

In Tables 1 and 2, a comparison between carrot variety NUN 89853 CAC and the Reference Variety (Rubyqueen) is shown based on a trial in the USA during the trial season 2018. Trial location: California, US; Harvest date: Feb. 14, 2018.

A trial of 30 plants of each variety, from which at least 15 plants or plant parts were randomly selected and were used to measure characteristics. For numerical characteristics, averages were calculated. For non-numerical characteristics, the type/degree were determined. In Tables 1 and 2, the descriptors of carrot variety NUN 89853 CAC and the Reference Variety are shown.

In one aspect, the disclosure provides a plant having the physiological and morphological characteristics of carrot variety NUN 89853 CAC as presented in Tables 1 and 2.

TABLE 1

Objective Description of Carrot Variety NUN 89853 CAC and the Reference Variety (USDA Descriptors); significant differences are highlighted in bold, where quantitative values are mentioned these are statistically significantly different between Carrot Variety NUN 89853 CAC and the Reference Variety using an ANOVA Tukey test.

| USDA Descriptors | NUN 89853 CAC | NUN 89849 CAC (Rubyqueen) |
|---|---|---|
| Type: | | |
| 1 = Amsterdam; 2 = Flakee; 3 = Berlicum; 4 = Chantenay; 5 = Danvers; 6 = Imperator; 7 = Nantes; 8 = Other (Specify) | Novel red type | Novel red type |
| Plant Top (at harvest stage): | | |
| Habit: 1 = Erect; 2 = Semi-erect; 3 = Prostrate | Semi-erect | Semi-erect |
| Plant Top Height (from Shoulder to Top of Crown), cm | 43.18 | 38.89 |
| Plant Top Neck Diameter, mm | 9.73 | 11.74 |
| Top Attachment: 1 = Single; 2 = Multiple | Single | Single |
| Leaf (at harvest stage): | | |
| Blade Color: 1 = Light Green; 2 = Medium Green; 3 = Dark Green; 4 = Other (Specify) | Medium green | Medium green |
| Color Chart Value (RHS Color Cart) | RHS N137B | N137A |
| Blade Divisions: 1 = Fine; 2 = Medium; 3 = Coarse | Medium | Medium |
| Blade Length (Without Petiole), cm | 21.44 | 17.30 |
| Petiole Length from Crown to First Pinna, cm | 29.31 | 23.25 |
| Petiole Anthocyanin: 1 = Absent; 2 = Present | Absent | Absent |
| Petiole Pubescence: 1 = Absent; 2 = Present | Present | Absent |
| Root (at market maturity): | | |
| Cortex Thickness (Midpoint X-Section), mm | 7.91 | 7.09 |
| Core Thickness (Midpoint X-Section), mm | 4.07 | 5.64 |
| Carrot Length (Minus Taproot), cm | 22.9 | 19.8 |
| Length of Taproot, mm | 36.61 | 50.23 |

TABLE 1-continued

Objective Description of Carrot Variety NUN 89853 CAC and the Reference Variety (USDA Descriptors); significant differences are highlighted in bold, where quantitative values are mentioned these are statistically significantly different between Carrot Variety NUN 89853 CAC and the Reference Variety using an ANOVA Tukey test.

| USDA Descriptors | NUN 89853 CAC | NUN 89849 CAC (Rubyqueen) |
|---|---|---|
| Diameter at Shoulder, mm | 24.09 | 26.76 |
| Diameter at Midpoint, mm | 20.39 | 23.32 |
| Amount Exposed (Above Ground):<br>1 = None; 2 = 1-10%; 3 = 11-20%; 4 = 21-30%; 5 = 31-40%; 6 = >40% | None | None |
| Shape: 1 = Round; 2 = Conic; 3 = Cylindrical | Cylindrical | Cylindrical |
| Collar: 1 = Sunken; 2 = Level; 3 = Square | Sunken | Level |
| Shoulder: 1 = Rounded; 2 = Sloping; 3 = Square | Rounded | Rounded |
| Base: 1 = Pointed; 2 = Medium; 3 = Blunt | Pointed | Pointed |
| Surface Smoothness:<br>1 = Very Smooth; 2 = Dimpled or Corrugated | More dimpled or corrugated | Dimpled or corrugated |
| Number of Secondary Root Scars:<br>1 = None; 2 = Few; 3 = Many | Many | Many |
| Appearance of Secondary Root Scars:<br>1 = Not Prominent; 2 = Prominent | Prominent | Prominent |
| Halo: 1 = None; 2 = Faint; 3 = Prominent | Prominent | Faint |
| Zoning: 1 = None; 2 = Faint; 3 = Prominent | Prominent | Prominent |
| Colors (RHS Colour Chart):<br>Color choices: 1 = white; 2 = yellow; 3 = orange; 4 = red; 5 = green;<br>7 = salmon; 8 = light; 9 = dark; 10 = other; color examples: 02 = yellow;<br>34 = orange-red; 94 = dark red | | |
| Below Ground Exterior Color: Shoulder | Light red (RHS 180A) | Dark red (RHS 173A) |
| Below Ground Exterior Color: Skin | Dark red (RHS 176A) | Dark red (RHS 173A) |
| X-Section Interior Color: Core | Red orange (RHS 178C) | Light red (RHS 173B) |
| X-Section Interior Color: Phloem | Dark red (RHS 176A) | Dark red (RHS 174A) |

TABLE 2

Objective Description of Carrot Variety NUN 89853 CAC and the Reference Variety (Non-USDA Descriptors); significant differences are highlighted in bold, where quantitative values are mentioned these are statistically significantly different between Carrot Variety NUN 89853 CAC and the Reference Variety using an ANOVA Tukey test.

| Non - USDA Descriptors | NUN 89853 CAC | NUN 89849 CAC (Rubyqueen) |
|---|---|---|
| Petiole Diameter, mm | 2.89 | 2.59 |
| Root Weight, grams | 67.60 | 85.20 |
| Brix (sugar content) | 10.80° | 11.45° |

The invention claimed is:

1. A carrot plant variety NUN 89853 CAC, or regenerable part thereof, wherein a representative sample of seed of said carrot variety is deposited under Accession Number NCIMB 43441.

2. A seed of variety NUN 89853 CAC, wherein a representative sample of seed of said carrot variety is deposited under Accession Number NCIMB 43441.

3. A plant or regenerable part thereof, produced by growing the seed of claim 2.

4. A plant part of claim 1, wherein the plant part is a leaf, a fruit, a root, a taproot, a cutting, a flower, or a cell.

5. The plant part of claim 4, wherein the plant part is a root.

6. A carrot plant or a part thereof having all of the physiological and morphological characteristics of the carrot plant of claim 1.

7. A tissue or cell culture of regenerable cells of the plant of claim 1.

8. The tissue or cell culture according to claim 7, comprising cells or protoplasts from a plant part, wherein the plant part is a meristem, a cotyledon, a hypocotyl, a seed coat, a leaf, an anther, a root, a root tip, a taproot, a pistil, a petiole, a flower, a fruit, a stem or a stalk.

9. A carrot plant regenerated from the tissue or cell culture of claim 7, wherein the plant has all of the physiological and morphological characteristics of the plant of claim 1, when grown under the same environmental conditions, and wherein a representative sample of seed of carrot variety NUN 89853 CAC has been deposited under Accession Number NCIMB 43441.

10. A method of producing the plant of claim 1 or a part thereof, comprising vegetative propagation of at least a part of carrot variety NUN 89853 CAC.

11. The method of claim 10, wherein said vegetative propagation comprises regenerating a whole plant from said part of carrot variety NUN 89853 CAC, wherein a representative sample of seed of said carrot variety has been deposited under Accession Number NCIMB 43441.

12. The method of claim 10, wherein said part is a cutting, a cell culture or a tissue culture.

13. A vegetative propagated plant of carrot variety NUN 89853 CAC, wherein the vegetative propagated plant has all of the physiological and morphological characteristics of the plant of carrot variety NUN 89853 CAC, when grown under the same environmental conditions, and wherein a representative sample of seed of carrot variety NUN 89853 CAC has been deposited under Accession Number NCIMB 43441.

14. A method of producing a carrot plant, comprising crossing the plant of claim 1 with a second carrot plant at least once, and selecting progeny from said crossing and optionally allowing the progeny to form seed, and wherein a representative sample of seed of carrot variety NUN 89853 CAC has been deposited under Accession Number NCIMB 43441.

15. A carrot plant having one physiological or morphological characteristic which is different from those of the plant of carrot variety NUN 89853 CAC and which otherwise has all the physiological and morphological characteristics of the plant of carrot variety NUN 89853 CAC, when grown under the same environmental conditions, and wherein a representative sample of seed of said carrot variety has been deposited under Accession Number NCIMB 43441, wherein said different characteristic is conferred by a transgene.

16. A single locus converted plant of carrot variety NUN 89853 CAC, having all of the morphological and physiological characteristics of the plant of carrot variety NUN 89853 CAC, wherein the single locus conversion is introduced by genetic transformation, and wherein a representative sample of seed of said carrot variety has been deposited under Accession Number NCIMB 43441, wherein the single locus conversion confers a trait of male sterility, herbicide tolerance, insect resistance, pest resistance, disease resistance, environmental stress tolerance, modified carbohydrate metabolism, or modified protein metabolism.

17. A method of producing doubled haploids of carrot variety NUN 89853 CAC, comprising making double haploid cells from haploid cells made from the plant or regenerable part thereof of claim 1 by chromosome doubling, and wherein a representative sample of seed of said carrot variety has been deposited under Accession Number NCIMB 43441.

18. A method of producing a carrot root comprising obtaining a plant according to claim 1, wherein the plant has been cultivated to maturity, and collecting the root from the plant.

19. A container comprising the seed of claim 2.

20. A container comprising the carrot root of claim 5.

21. A container comprising the carrot root collected in the method of claim 18.

22. A food or a feed product comprising the carrot root, or parts thereof, of claim 5.

23. A method of producing a carrot plant having a trait, wherein the method comprises mutating a carrot plant of variety NUN 89853 CAC and selecting a mutated plant with a different trait, wherein the mutated plant retains all of the physiological and morphological characteristics of carrot variety NUN 89853 CAC, when grown under the same environmental conditions and contains the different trait and wherein a representative sample of seed of said carrot variety has been deposited under Accession Number NCIMB 43441.

* * * * *